United States Patent
Lantz et al.

(10) Patent No.: US 10,085,819 B2
(45) Date of Patent: Oct. 2, 2018

(54) DENTAL DRILL SYSTEM

(71) Applicant: Elos Medtech Timmersdala AB, Timmersdala (SE)

(72) Inventors: Mattias Lantz, Mariestad (SE); Per-Olof Karlsson, Alingsås (SE)

(73) Assignee: Elos Medtech Timmersdala AB, Timmersdala (SE)

( * ) Notice: Subject to any disclaimer, the term of this patent is extended or adjusted under 35 U.S.C. 154(b) by 0 days.

(21) Appl. No.: 14/911,131

(22) PCT Filed: Aug. 25, 2014

(86) PCT No.: PCT/SE2014/050967
§ 371 (c)(1),
(2) Date: Feb. 9, 2016

(87) PCT Pub. No.: WO2015/030652
PCT Pub. Date: Mar. 5, 2015

(65) Prior Publication Data
US 2016/0199151 A1    Jul. 14, 2016

(30) Foreign Application Priority Data
Aug. 26, 2013 (SE) ...................................... 1350973

(51) Int. Cl.
*A61C 1/08* (2006.01)
*A61C 8/00* (2006.01)
*A61C 3/02* (2006.01)

(52) U.S. Cl.
CPC ............... *A61C 1/084* (2013.01); *A61C 1/082* (2013.01); *A61C 3/02* (2013.01); *A61C 8/0089* (2013.01)

(58) Field of Classification Search
CPC ......... A61C 1/084; A61C 1/082; A61C 1/085; A61C 3/02; A61C 8/0089;
(Continued)

(56) References Cited

U.S. PATENT DOCUMENTS 4,998,881 A * 3/1991 Lauks ................... A61C 1/084
   433/173
5,350,297 A    9/1994 Cohen
(Continued)

FOREIGN PATENT DOCUMENTS

CN    103156692 A    6/2013
CN    103260542 A    8/2013
(Continued)

OTHER PUBLICATIONS

International Search Report for PCT/SE2014/050967 dated Dec. 11, 2014.
(Continued)

*Primary Examiner* — Nicholas Lucchesi
*Assistant Examiner* — Shannel Wright
(74) *Attorney, Agent, or Firm* — Alston & Bird LLP (57) ABSTRACT

A dental drill system is provided, comprising a drill having a drilling part with a first end configured for drilling a hole in a jaw bone and a shank part with a second end configured for connection to a drill-rotating device and a guiding sleeve for guiding the drill. The guiding sleeve has a first side facing the drill-rotating device and a second side intended to face the jaw bone during a drilling operation. A guiding through-hole extends from the first side to the second side. A rim also extends at least partly around the circumference of the drill, and the system comprises a drill stop sleeve provided with a recess extending circumferentially around an inner side of the drill stop sleeve, allowing the drill stop sleeve to be snap-locked onto the drill. The guiding sleeve also comprises a flange that defines an end position for the drill stop sleeve.

18 Claims, 9 Drawing Sheets

(58) Field of Classification Search
CPC ........ A61B 17/32052; A61B 17/32053; A61B 17/1673; A61B 2090/036; A61B 2090/034; A61B 17/176; A61B 17/1633; A61B 17/1604; Y10T 408/99
USPC .................................. 433/75, 76; 606/80, 96
See application file for complete search history.

(56) References Cited

U.S. PATENT DOCUMENTS

| | | | | |
|---|---|---|---|---|
| 5,488,958 | A | * | 2/1996 | Topel ............. A61B 17/320016 600/567 |
| 5,743,916 | A | * | 4/1998 | Greenberg ............. A61B 17/02 606/102 |
| 5,782,853 | A | | 7/1998 | Zeevi et al. |
| 6,110,178 | A | * | 8/2000 | Zech ................... A61B 17/1635 606/96 |
| 6,146,385 | A | | 11/2000 | Torrie et al. |
| 6,514,258 | B1 | * | 2/2003 | Brown ................... A61C 1/084 408/202 |
| 6,916,322 | B2 | * | 7/2005 | Jesch ................ A61B 17/1637 433/165 |
| 6,942,669 | B2 | * | 9/2005 | Kurc ................... A61B 17/1635 606/80 |
| 6,971,877 | B2 | | 12/2005 | Harter |
| 7,942,668 | B2 | | 5/2011 | Brajnovic et al. |
| 8,777,613 | B2 | | 7/2014 | Wolf et al. |
| 8,794,963 | B2 | | 8/2014 | Lancieux et al. |
| 9,211,126 | B2 | | 12/2015 | Sikora et al. |
| 9,615,841 | B2 | * | 4/2017 | Eder ................... A61B 17/176 |
| 2004/0219479 | A1 | * | 11/2004 | Malin ................... A61C 1/084 433/75 |
| 2004/0219480 | A1 | | 11/2004 | Malin |
| 2004/0219481 | A1 | | 11/2004 | Malin et al. |
| 2004/0236214 | A1 | | 11/2004 | Opie et al. |
| 2005/0170311 | A1 | * | 8/2005 | Tardieu ................. A61C 1/084 433/76 |
| 2006/0291968 | A1 | * | 12/2006 | Greenberg ............. A61C 1/084 408/202 |
| 2007/0203500 | A1 | | 8/2007 | Gordon et al. |
| 2008/0177266 | A1 | | 7/2008 | Metcalf et al. |
| 2008/0220390 | A1 | * | 9/2008 | Klein ................... A61C 1/084 433/76 |
| 2009/0181340 | A1 | * | 7/2009 | Wolf ................... A61C 1/084 433/76 |
| 2010/0062389 | A1 | * | 3/2010 | Drews ................. A61B 17/176 433/75 |
| 2010/0129768 | A1 | | 5/2010 | Isidori |
| 2010/0151412 | A1 | * | 6/2010 | Suter .................... A61C 8/0089 433/75 |
| 2010/0311006 | A1 | * | 12/2010 | Lancieux ............... A61C 1/084 433/75 |
| 2011/0054483 | A1 | * | 3/2011 | Howlett ............ A61B 17/1617 606/96 |
| 2011/0059419 | A1 | * | 3/2011 | Fujii .................... A61C 8/0089 433/144 |
| 2011/0177469 | A1 | | 7/2011 | Suter et al. |
| 2011/0256500 | A1 | * | 10/2011 | Crudo .................... A61C 1/084 433/75 |
| 2011/0270236 | A1 | * | 11/2011 | Eder .................. A61B 17/1673 606/3 |
| 2012/0067189 | A1 | | 3/2012 | Kraft et al. |
| 2012/0109140 | A1 | | 5/2012 | Akutsu |
| 2013/0084540 | A1 | * | 4/2013 | Yoshihara ............ A61C 8/0089 433/75 |
| 2013/0157219 | A1 | | 6/2013 | Lo et al. |
| 2013/0344453 | A1 | | 12/2013 | Eder |
| 2014/0046123 | A1 | | 2/2014 | Connors et al. |
| 2015/0342680 | A1 | | 12/2015 | Schneider |

FOREIGN PATENT DOCUMENTS

| | | | |
|---|---|---|---|
| EP | 1759658 A1 | 3/2007 | |
| EP | 2 572 671 A1 | 3/2013 | |
| EP | 2381857 B1 | 7/2013 | |
| ES | 1069431 U | 3/2009 | |
| JP | 2009-207659 A | 9/2009 | |
| WO | WO 2004/098435 A2 | 11/2004 | |
| WO | WO 2007065978 A1 * | 6/2007 | ............. A61B 17/17 |
| WO | WO 2009/071885 A1 | 6/2009 | |
| WO | WO 2009071885 A1 * | 6/2009 | ........... B23B 49/005 |
| WO | WO 2010/049031 A1 | 5/2010 | |

OTHER PUBLICATIONS

European Patent Office, Extended European Search Report for Application No. 14839568.4, dated Mar. 7, 2017, 7 pages, Germany.
International Searching Authority, International Preliminary Report on Patentability for International Application No. PCT/SE2014/050967, dated Dec. 11, 2014, 4 pages, Swedish Patent and Registration Office.
State Intellectual Property Office of the P.R.C., First Office Action for Application No. 201480047132.8, dated Nov. 28, 2017, 13 pages, China.

* cited by examiner

DENTAL DRILL SYSTEM

CROSS REFERENCE TO RELATED APPLICATIONS

This application is a U.S. National Phase Application of PCT International Application Number PCT/SE2014/050967, filed on Aug. 25, 2014, designating the United States of America and published in the English language, which is an International Application of and claims the benefit of priority to Swedish Patent Application No. 1350973-2, filed on Aug. 26, 2013. The disclosures of the above-referenced applications are hereby expressly incorporated by reference in their entireties.

TECHNICAL FIELD

The invention relates to a dental drill system, comprising a drill having a drilling part with a first end configured for drilling a hole in a jaw bone and a shank part with a second end configured for connection to a drill-rotating device, and a guiding sleeve for guiding the drill during drilling. The guiding sleeve has a first side intended to face the drill-rotating device and a second side intended to face the jaw bone during a drilling operation. A guiding through-hole extends from the first side to the second side of the guiding sleeve.

BACKGROUND

Dental surgery, such as replacing a tooth with an implant commonly is complicated and involves many steps and procedures. Once the old tooth is removed the replacement with an implant commonly involve the steps of making a gypsum or plastic model of the adjacent teeth, arranging a guide in the stent, punching the gum tissue to expose the jawbone in the area of the missing tooth, placing the stent with the drill guide over the exposed area and drilling a hole into the bone in which the implant is to be arranged and installing the implant or an anchoring member. Typically, the actual crown, such as a prosthetic tooth or a bridge, is arranged into the implant or anchoring member several months later once the gum and bone have healed. Hence, it is beneficial if the punched hole is as tight around the upcoming drilling hole as possible such that less stitching and healing is needed. It is also preferred if the drilling itself is as accurate and as possible to decrease the impact of the tissue and bone. Therefore drilling guides may be used to guide the drill during drilling of the hole in the jaw bone.

WO04/098435 discloses a method for arranging a drill bushing in a stent. The drill bushing may also function as guide for a tissue puncher wherein the tissue puncher comprises a tissue punch tube, a tissue punch elongated tooth and a tissue punch cutting point. The tissue punch generates tissue holes through rotation of the tissue punch cutting point and the punching is thereby more controlled than if cutting was done by hand.

Generally a lot of different tools are needed during dental surgery, and there is a need for improved systems which comprise fewer tools with fewer individual parts in order to simplify the procedure for the dental surgeon. There is also a need for more accurate tools which generates less damage during the procedure such that the pain a patient is subjected to is reduced.

SUMMARY

The object of the invention is to provide an improved dental drilling system for dental surgery which provides high accuracy during use and is also simple to use. The object is achieved by the system of claim 1.

The invention concerns a dental drill system comprising a drill having a drilling part with a first end configured for drilling a hole in a jaw bone and a shank part with a second end configured for connection to a drill-rotating device. It also comprise a guiding sleeve for guiding the drill during drilling, wherein the guiding sleeve has a first side intended to face the drill-rotating device and a second side intended to face the jaw bone during a drilling operation, and wherein a guiding through-hole extends from the first side to the second side.

According to the invention a rim extends at least partly around the circumference of the drill, and the system comprises a drill stop sleeve that is capable of being brought onto the drill. The drill stop sleeve is provided with a recess extending circumferentially around an inner side of the drill stop sleeve, wherein the relative dimensions of the rim and the recess are adapted to allow the drill stop sleeve to be snap-locked onto the drill. Thereby the drill stop is easily fitted onto the drill, and is also easily removed from the drill by the snap-lock function which allows it to "snap-off". Moreover the guiding sleeve comprises a flange that defines an end position for the drill stop sleeve, i.e. the flange prevents the drill stop sleeve and thereby the drill from being moved further through the guiding sleeve towards the jaw bone.

Such a system has the advantageous effect that, besides the guiding of the direction of the drill provided by the guiding sleeve, which typically is secured in proper alignment with the patient's jaw bone in a plastic dental template (a stent), the end position of the drill stop sleeve sets the depth of the drilled hole and eliminates the risk of drilling too deep into the jaw bone. This way the drilling operation becomes more safe and easy to perform.

Moreover, because the snap-lock function makes the drill stop sleeve removable it is possible to make use of a set of drill stop sleeves of varying length, each of which being adapted to fit on the same drill by adapting the relative dimensions of the drill rim and the recess of the drill stop sleeves of varying length. This way it is possible to avoid having a large set of drills with integrated drill stops to choose from for a certain intended drill depth. The snap-on function also makes it quick and easy for the dentist to change the drill stop if there is a need to use several drill depths with the same drill during the procedure. Such drill stop sleeves can be made in a plastic material and are much less costly than dental drills. The system according to the invention is thus more cost-effective than systems using different drills with integrated drill stops.

The drill stop sleeve may be brought onto the drill from the second end towards the drilling part, or from the first end towards the shank. It is beneficial to bring the drill stop sleeve onto the drill from the second end because it allows the same drill stop sleeve to be used with different drills with the same shank diameter but of varying lengths or bore diameters. The shank diameter of drills and the snap-lock portion of drill stop sleeves may be standardized.

Further, since the recess is provided onto the drill stop sleeve and the rim onto the drill, and not vice versa, the risk of the drill stop sleeve getting stuck at the second end of the drill, which usually is provided with a recess for connection to the drill-rotating device, is avoided.

The snap-lock function of the drill stop sleeve may allow the drill to rotate even if the drill stop sleeve is held still against the guiding sleeve. In another aspect of the invention the drill stop sleeve may rotate with the rotation of the drill.

The sleeve part of the drill stop sleeve, extending over the drilling part of the drill, is therefore arranged to fit snugly around the drilling part such that a large gap between the sleeve and the drill is avoided but a small gap is still present to allow the drill sleeve part to rotate around the drilling part without abutting.

The drill stop sleeve may have cut outs arranged circumferentially and extending perpendicular to the circumferential recess. The cut outs may extend from a first end of the drill stop sleeve, the first end being located near the recess, towards the body of the drill stop sleeve. The cut outs are preferably arranged opposite each other. The number of cut outs may vary, any suitable number of cut outs is possible. The cut outs facilitate flexing of the snap-lock part, being the part of the drill stop sleeve where the recess and cut outs are arranged, such that the drill stop sleeve may be arranged upon a rim of a drill.

In an embodiment of the invention the rim is positioned on the shank part of the drill. Thereby, drills of different bore diameters may still have rims of the same diameter; a rim diameter that is the same as the one of the recess extending circumferentially around an inner side of a drill stop sleeve such that the drill stop sleeve fits different drills independent of their bore diameters.

Some drills according to the invention will have a diameter of the rim that is less than the diameter of the bore part of the drill. Such drills may be used also for drilling by hand without a drill stop sleeve attached, eliminating the risk that the rim abuts the edge of the drill hole as the drill hole deepens. Hence, such an embodiment of the drill is versatile as the drill may be used with or without the drill stop sleeve snap-locked onto it.

According to one aspect of the invention the rim is positioned closer to the drilling part of the drill than to the second end of the shank part. The position of the rim allows the drill stop sleeve to be snap-locked in a position close to the drilling part. A waist may be formed in between the rim and the drilling part of the drill. The waist may be used for colour labelling the drill such that it is easily matched with a colour labelled drill stop sleeve.

In an aspect of the invention the drill stop sleeve is made of a high temperature resistant thermoplastic material, such as polypohenylsulfone or preferably polyoximetylen. Such material is highly resistant to steam autoclaving and thus suitable for dental product. The material also makes the drill stop sleeve resistant to impact. A drill stop sleeve of such a material is therefore reusable and cost-effective.

In another aspect of the invention a portion of the guiding through-hole at its first side of the guiding sleeve is adapted to receive the drill stop sleeve, and the flange that defines the end position for the drill stop sleeve is arranged inside the guiding sleeve such as to form an end of said portion of the guiding through-hole.

Such a design has the advantage that the drill comes closer to the jaw bone than if the drill stop sleeve would press onto and be stopped by the outer surface of the first part of the guiding sleeve. In turn this has the effect that the use of extra-long drills can be avoided, i.e. the same drill (with rim) can be used both for free-hand drilling, if preferred, as well as in the inventive system with guiding sleeve and drill stop sleeve. Again, this reduces the complexity of the required equipment and makes the system cost-effective. The deeper the drill and the drill stop sleeve are allowed to be inserted through the guiding sleeve, i.e. the shorter the distance between the flange and the outer side of the second part of the guiding sleeve, the shorter drill can be used.

In an embodiment of the invention the flange is positioned closer to the second side of the guiding sleeve than the first side of the guiding sleeve. This means that the drill stop sleeve is received by at least half the length of the guiding through-hole when the drill stop sleeve is at its end position.

By allowing the drill stop sleeve to be received in the guiding sleeve and arranging the flange such that the drill stop sleeve enters over half of the depth of the guiding sleeve before abutting the flange the drill stop sleeve is stably positioned at its end position which thereby facilitates accurate and precise drilling. Another advantage is that more of the drill length is protruding from the guiding sleeve as the drill stop sleeve is allowed to be received in the guiding sleeve. More of the length of the drill may thereby be used for drilling as opposed to being enclosed by the guiding sleeve as in systems in which the drill stop sleeve is abutting the an outer surface of the guiding sleeve. Thereby, a shorter drill may be used for deeper drilling which may result in less drill changes i.e. less effort for the dental surgeon.

In an embodiment of the invention the guiding sleeve comprises an outer sleeve element and an inner sleeve element, wherein the inner sleeve element fits into and is securable in the outer sleeve element and wherein the inner sleeve element is provided with the drill guiding through-hole and the flange. The outer sleeve element comprises a through-hole in which the inner sleeve element is adapted to fit. This means that the drill stop sleeve is received by the inside of the inner, separate, sleeve element which thus forms a sort of adapter element. Such a design is useful for adapting the guiding sleeve, i.e. adapting the inner sleeve element of the guiding sleeve, to drills and drill stop sleeves of different diameters. Thereby, one outer sleeve element may be used with several drills of different bore diameters during one operation by simply varying the inner sleeve element such that the guiding sleeve fits several drills and drill stop sleeves.

The system may comprises a punching sleeve having a cutting end part suitable for removal of tissue on a jaw bone of a patient, wherein the punching sleeve forms the inner sleeve element of the guiding sleeve. This means that the punching sleeve forms part of the guiding sleeve by forming also the adapter element provided with the guiding through-hole and the flange that defines an end position for the drill stop sleeve. The punching sleeve is thus adapted to fit inside and be guided along the outer sleeve element. The cutting end part of the punching sleeve may however be of a different diameter than the inner sleeve element which fits in the outer sleeve element like an adapter element. Thereby the size of the incision is controlled by the diameter of the cutting end part and not by the outer diameter of the inner sleeve element. These can of course also have the same diameter.

The flange arranged in the through-hole of the punching sleeve allows the punching sleeve to receive the drill stop sleeve, thereby giving the system the advantage of facilitating the use of shorter drills for the same drill depths. Shorter drills are commonly easier to handle for the dental surgeons.

The punching sleeve may be adapted to be guided by the outer sleeve element when the punching sleeve is moved in an axial direction in relation to the outer sleeve element. Such an arrangement allows for punching to be performed with high precision and accuracy which eliminates the risk of a long recovery after uncontrolled cutting or unguided punching of the tissue. A distinct incision edge is facilitated by allowing the punching sleeve to be guided such that the cutting end part enters and exits the tissue in a controlled manner. By improving the precision of the punching a smaller tissue area may be punched compared to punching by hand only.

The cutting end part of the punching member comprises means for cutting through tissue. Examples include but are not limited to a continuous sharp edge or a saw toothed edge.

In one aspect of the invention the punching sleeve and the outer sleeve element are provided with complementary guiding means configured to control the axial movement of the punching member in the outer sleeve element during the punching operation, wherein the complementary guiding means comprise at least one guiding element that extends in a radial direction and at least one guiding groove adapted to receive the guiding element and guide its movement along the guiding groove, and wherein the guiding groove extends both in a circumferential direction as well as in an axial direction such that, when the guiding element and the guiding groove are engaged, a rotation of the punching sleeve in relation to the outer sleeve element forces the punching member to move in relation to the outer sleeve element in the axial direction thereof.

Thus, the interaction between the guiding element and the guiding groove during rotation of the punching sleeve forces the punching sleeve to move axially through the guiding through-hole. By giving the outer end of the punching sleeve, i.e. the non-cutting end part, a suitable form for gripping, or by using a specially adapted tool connectable to the punching sleeve, it is possible to achieve a very distinct but at the same time controlled axial movement that provides for an efficient punching operation. The punching sleeve can be moved in the opposite direction simply by rotating it in the opposite direction. That way, the punching sleeve can also be removed from the outer sleeve element after use.

In one aspect of the invention the at least one guiding element extends in a radial direction either from an inside of the guiding sleeve, if arranged onto the guiding sleeve, or from an outside of the punching member, if arranged onto the punching member. In this aspect the at least one guiding groove is arranged either on an outer side of the punching member, if the guiding element is arranged onto the guiding sleeve, or on the inside of the guiding sleeve, if the guiding element is arranged onto the punching member. Further, the guiding groove extends circumferentially and axially along the part it is arranged to.

The guiding element is preferably in the form of a pin. A pin simplifies the fitting of the guiding element, the pin, in the guiding groove as well. It is also simple to make. The guiding element may comprise at least two pins arranged circumferentially in a radial direction either from an inside of the guiding sleeve or from an outside of the punching member and the guiding groove may thus comprise at least to complementary grooves extends circumferentially and axially along the part it is arranged to. Other types of complementary guiding means are also possible e.g. the guiding element may be threaded wherein the thread is adapted to engage in a guiding groove slot which is complementary threaded. Such an alternative also allows the guiding element to slide in the guiding groove when the punching member is rotated and hence facilitated controlled axial movement of the punching member in the guiding sleeve.

The groove may be a slit extending through the entire radial extension of the member on which it is arranged.

In another aspect of the invention the outer sleeve element is provided with the guiding element and the punching sleeve provided with the guiding groove. One benefit with such a design is that it is simple to carve a groove at the outside of the punching sleeve. Hence such a design is simple to manufacture. Also, such a punching sleeve may be used, if needed, to punch gums without the complementary outer sleeve element because it does not comprise any protruding guiding elements. A punching sleeve provided with a guiding groove is therefore versatile in terms of use.

A pin-shaped elongated element may be arranged to extend in radial direction through a hole arranged through the outer sleeve element body such that a tip of the pin-shaped elongated element protrudes on the inside of the outer sleeve element, wherein said tip forms the guiding element. One advantage of such a design is that it is easy to provide the outer sleeve element body with a radially extending hole and subsequently easy to arrange a pin-shaped elongated element through such a hole. The pin-shaped elongated element may for example be a screw and the hole in the guiding sleeve may thus comprise threads such that the screw may be easily and securely arranged in the hole.

The invention may be further improved by providing the closed end of the guiding groove with an additional extension with a different direction of extension, i.e. a change in vertical or horizontal direction of extension. One example of a closed end is a distinct bend to the guiding groove. Thereby, the axial end position of the punching member may be easily identified by a change in rotational movement of the punching member facilitated by the guiding element sliding in the guiding groove. Such an improved closed end also facilitates that the punching sleeve remains in its end position until a deliberate motion displaces it from the axial end position by moving the guiding element out of the closed end of the guiding groove.

Alternatively, the depth of the punched hole can be controlled by providing the system with another element that defines an end position for the punching sleeve. For instance, this can be arranged by providing a flange inside the guiding through hole that interacts with a corresponding surface or flange of the punching sleeve, or by providing a flange on the punching sleeve that interacts with first side of the outer sleeve element thereby defining the punching sleeves end position.

If the present invention is provided with a punching sleeve the dental drill system is given double function, because the punching sleeve may function both as a punch and as a drill guide sleeve. An advantage with the system is hence that the punching sleeve does not have to be removed from the guiding sleeve prior to drilling. In addition, the drill will be guided all the way through the gum tissue towards the jaw bone because the punching sleeve extends through the gum tissue. A single guiding sleeve of common design, without an inner sleeve, does not guide through the gums. Therefore, the guiding of the drill is improved with the system according to the present invention.

In another aspect of the invention the punching sleeve is provided with a first and second circumferentially spaced engagement member intended for engagement with a rotational tool. The rotational tool is used to facilitate a controlled rotation of the punching sleeve but the rotation may also be done by hand. The engagement members ensure that the rotational tool is securely fastened when being used and the engagement members may be arranged on the inside of the through-hole of the punching sleeve or on the outside of the punching sleeve.

The dental drill system may further comprise a rotational tool adapted to engage with the punching sleeve. The rotational tools thus have complementary engagement means adapted to engage with the engagement members of the punching member.

The punching sleeve may be left in place in the outer sleeve element of the guiding sleeve after use such as to form a guide for the drill and the drill stop sleeve. Such a design makes the punching and drilling operation simple and efficient when carried out consecutively.

After completion of punching the punching sleeve may be removed from the outer sleeve element by a counteracting motion. Alternatively the rotational tool used during the rotational movement of the punching sleeve may be disengaged from the punching sleeve such that the punching sleeve is left in the outer sleeve element.

The guiding sleeve and the punching sleeve are preferably made of a metallic material which makes them sustainable and resistant. They are also easily sterilized such that they may be reused.

BRIEF DESCRIPTION OF THE DRAWINGS

The present invention will now be described in detail with reference to the figures, wherein:

FIG. 4b shows a cross section view of the drill stop sleeve of FIG. 4a;

FIG. 8b shows a cross section of a perspective view of the rotational tool engaged to the inner sleeve element of FIG. 1.

DETAILED DESCRIPTION OF THE DRAWINGS

In the following only one embodiment of the invention is shown and described, simply by way of illustration of one mode of carrying out the invention.

Figure 1:
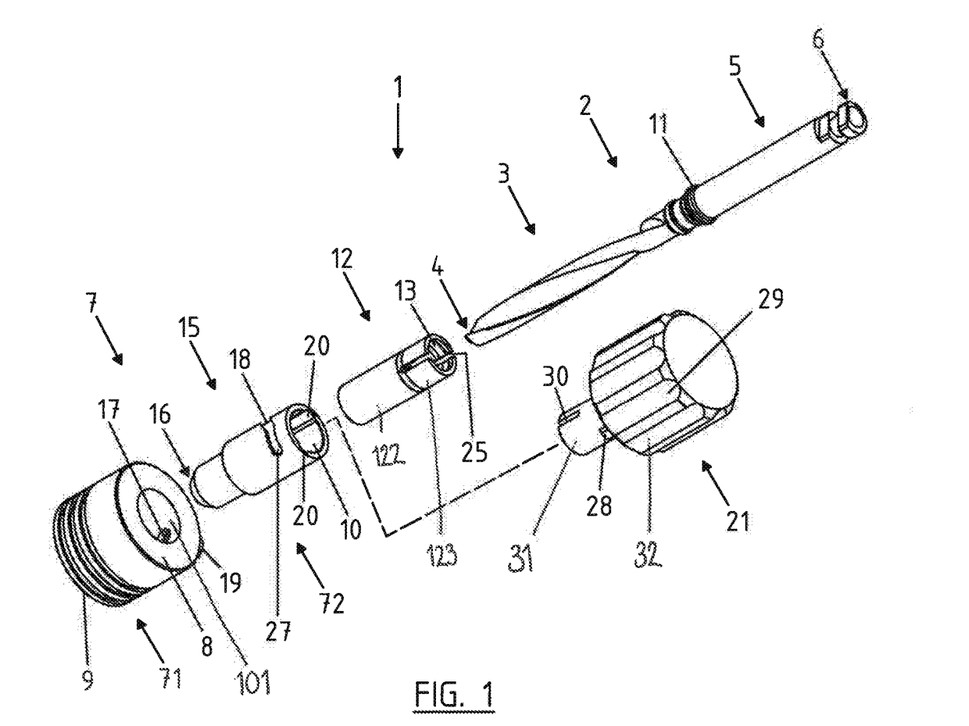
FIG. 1 shows one embodiment of the dental drill system according to the invention.

FIG. 1 shows an example of a dental surgery device 1 according to the invention. The parts of the dental surgery device; a drill 2, a drill stop sleeve 12, a guiding sleeve 7, comprising an inner sleeve element 72 and an outer sleeve element 71, and a rotational tool 21, are lined up in an exemplified order of assembly (before use). The drill 2 has a drilling part 3 with a first end 4 configured for drilling a hole in a jaw bone. The choice of drill diameter may be adapted to the situation, e.g. to the implant intended to be applied. The drill 2 also has a shank part 5 with a second end 6 configured for connection to a drill-rotating device. A rim 11 extends around the circumference of the shank part 5 of the drill 2. The rim 11 is positioned close to the drilling part 3 of the drill 2, i.e. closer to the drilling part 3 than to the second end of the shank part 5.

The drill stop sleeve 12 is of cylindrical shape and has a hollow interior extending through the length of drill stop sleeve 12. The drill stop sleeve 12 has a snap-lock part 123, comprising a recess 13 extending circumferentially around an inner side of the drill stop sleeve 12, and a sleeve part 122. The recess 13 is adapted to fit around the rim 11 of the drill 2. The sleeve part 122 is intended to extend circumferentially over the drilling part 3 of the drill 2 once the drill stop sleeve 12 has snap-locked upon the drill 2. The sleeve part 122 is arranged to fit snugly around the drilling part 3 of the drill 2.

The drill stop sleeve 12 in FIG. 1 also has two cut outs 25 arranged circumferentially opposite each other extending perpendicular to the circumferential recess 13 going through the sleeve at the snap-lock part 123 of the drill stop sleeve 12. The cut outs 25 allow the snap-lock part 123 of the drill stop sleeve 12 to flex such that it may be brought over the rim 11 of the drill 2.

In the example shown FIG. 1 the diameter of the drilling part 3 of the drill 2 is sufficiently small to allow the drill stop sleeve 12 to be brought onto the drill 2 from the first end 4. The drill stop sleeve 12 may also be brought onto the drill 2 from the second end 6 towards the drilling part 3 such that the snap-lock part of the drill stop sleeve 12 snap-locks onto the drill 2 by allowing the recess 13 of the drill stop sleeve 12 to engage with the rim 11 on the shank part 5 of the drill 2.

Figure 4A:
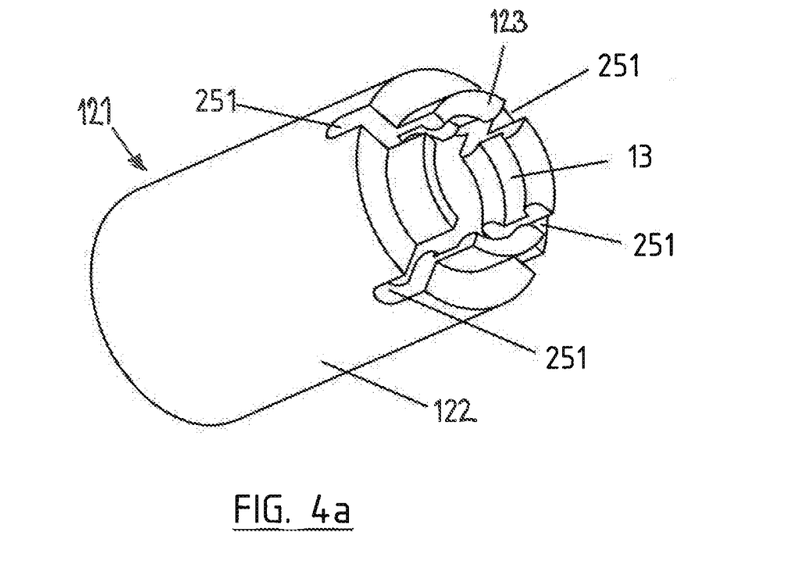
FIG. 4a shows a perspective view of an alternative drill stop sleeve.
Figure 4B:
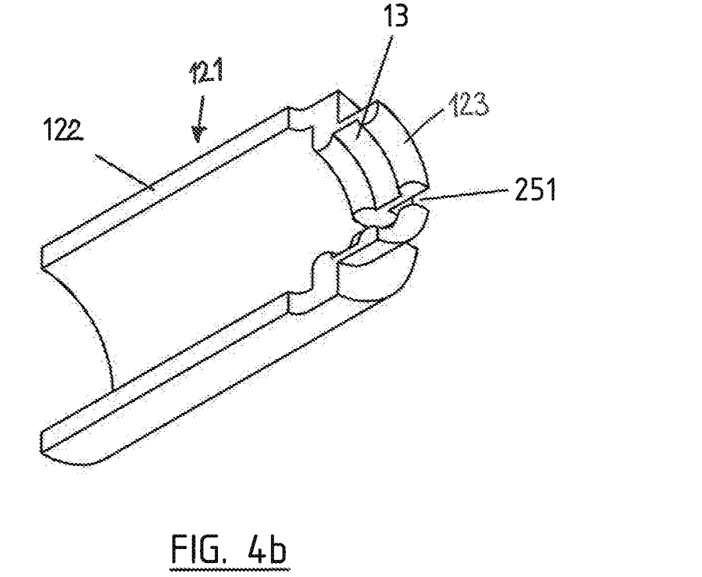

Another example of a drill stop sleeve 121 in seen in FIG. 4a-b. The sleeve part 122 of the drill stop sleeve 121 has in this case a larger diameter than the snap-lock part 123 thereby enabling the sleeve part 122 to fit a drill 2 of a larger bore diameter, i.e. comprising a drilling part 3 which is wider than the shank part 5. The drill stop sleeve 121 is provided with four cut outs 251 evenly spaced along the circumference of the drill stop sleeve 121 such that the cut outs 251 are arranged in two pairs and wherein the cut-outs 251 of each pair are arranged opposite each other. The cut outs 251 extend from the edge of the snap-lock part 123 of the drill stop sleeve 121, across the snap-lock part 123 and towards the sleeve part 122 of the drill stop sleeve 121. The number of cut-outs 251 and the extension of the cut-outs 251 in vertical direction may of course vary.

During assembly the drill stop sleeve 12 may be brought onto the drill 2 from the second end 6 towards the drilling part 3 such that the snap-lock part 123 of the drill stop sleeve 12 snap-locks onto the drill 2 by allowing the recess 13 of the drill stop sleeve 12 to engage with the rim 11 on the shank part 5 of the drill 2. The diameter of the recess 13 and the diameter of the rim 11 are configured relative each other such that the drill stop sleeve 12 may be securely arranged to snap-lock upon the drill 2 and securely lock the position of the drill stop sleeve 12.

Figure 2:
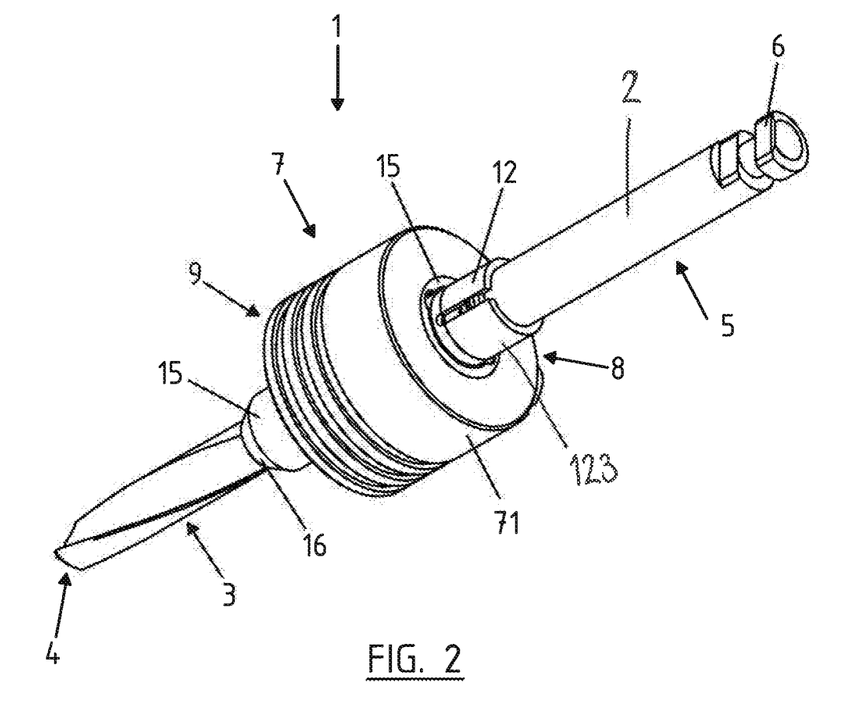
FIG. 2 shows the embodiment of FIG. 1 when assembled.
Figure 3:
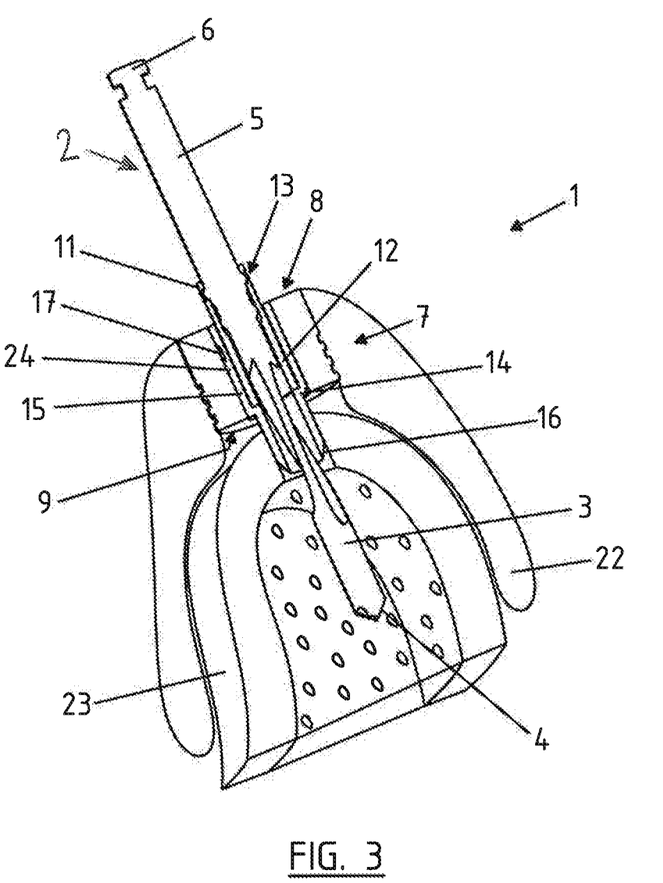
FIG. 3 shows a cross section of the embodiment of FIG. 1 when in use.

The inner sleeve element 72 is exemplified as a punching member 15 having the shape of a hollow circular cylinder and arranged to fit in the outer sleeve element 71. The punching member 15 is provided with a cutting part 16, intended to face the jaw bone during a punching operation, and a sleeve part 160. The diameter of the cutting part 16 is less than the diameter of the sleeve part 160. During use, the cutting part 16 protrudes from the second part 9 of the outer sleeve element 71 whereas the sleeve part 160 is arranged inside the outer guiding element 71, as shown in FIGS. 2-3. The outer sleeve element 71 has a through-hole 101 with an inner diameter adapted to the outer diameter of the punching member 15.

Figure 5:
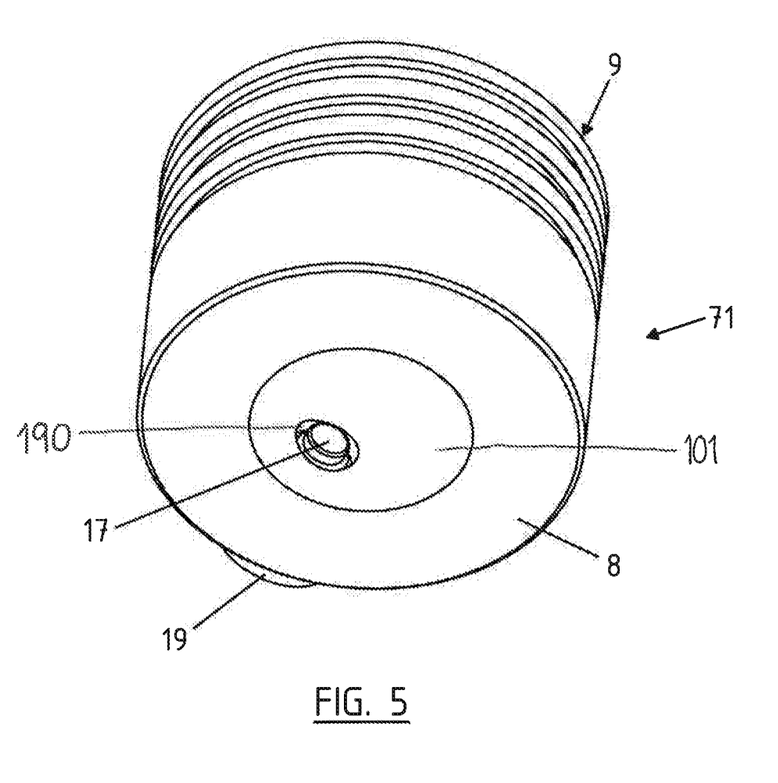
FIG. 5 shows a perspective view of the outer sleeve element of FIG. 1.

The outer guiding element 71 is provided with a pin-shaped elongated element 19, in the form of a screw, which extends in a radial direction through a thread-provided, radial extending, hole 190 arranged through a wall of the outer sleeve element 71. The tip of the pin-shaped elongated element 19 protrudes on the inside of the outer sleeve element 71 such that it forms the guiding element 17, seen in FIG. 5. Thereby the guiding element 17 is easily arranged upon the outer sleeve element 71.

Figure 6A:
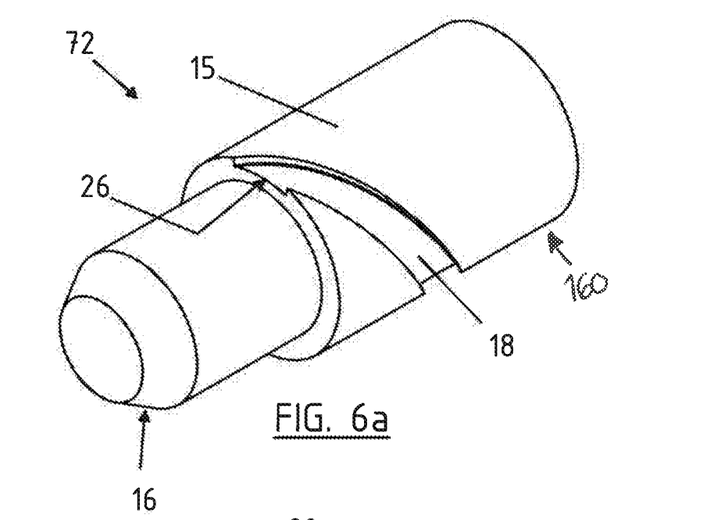
FIG. 6a-c shows a perspective view of the inner sleeve element of FIG. 1.
Figure 6B:
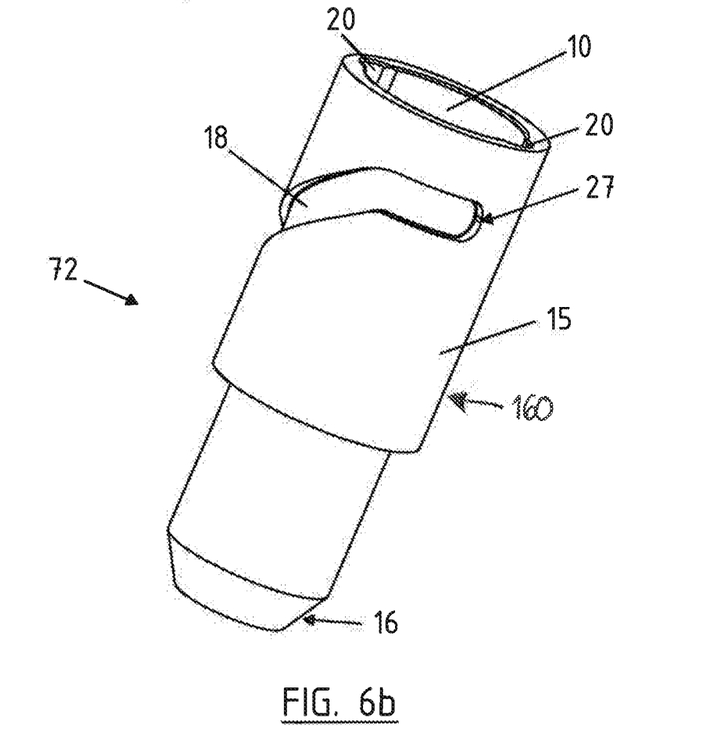

The punching member 15 is provided with a guiding groove 18 in the form of a recess that extends both in a circumferential direction as well as in an axial direction, in a helical manner, along the outer surface of the punching member 15, specifically on the sleeve part 160. The guiding groove 18 is provided with an open end 26 (see FIG. 6*a*) that allows introduction of a protruding pin-shaped elongated element 19 of the outer sleeve element 71 into the guiding groove 18 and a closed end 27 (see FIGS. 1 and 6*b*) that prevents further movement of the guiding element 17 along the guiding groove 18 upon rotational movement of the punching member 15 relative the outer sleeve element 71. The open end 26 of the guiding groove 18 is open towards the edge of the sleeve part 160 facing the cutting part 16. The guiding groove 18, starting from the open end 26, extends both in a circumferential direction as well as in an axial direction towards the closed end 27 with a pitch angle of about 30°. The exact angle and path of the guiding groove 18 may be adapted to the particular application.

A part, an additional extension, of the guiding groove 18 adjacent the closed end 27 is essentially horizontal, i.e. it extends only circumferentially and not axially such that the pitch angle becomes zero. Thereby, the axial movement of the punching member 15 relative the outer sleeve element 7 is stopped once the guiding pin 17 reaches the part adjacent the closed end 27 of the guiding groove 18. The punching member 15 may be left in this position, being the end position of the axial movement.

The movement of the guiding element 17 in the guiding groove 18, together making up the complementary guiding means, controls the axial movement of the punching member 15 relative the outer sleeve element 71, consequently controlling axial movement of the cutting edge 16 into the tissue. The angle and path of the guiding groove 18, together with the rotational speed and torque, thereby controls the punching operation.

When the punching member 15 is inserted into the outer sleeve element 71 it is rotationally adjusted so that the guiding element 17 i.e. the tip of the pin-shaped elongated element 19, enters the open end 26 of the guiding groove 18. When the punching member 15 at that point is rotated, e.g. by using the tool 21, the guiding element 17 will follow the path defined by the guiding groove 18. Since this path extends both circumferentially around the punching member 15 as well as axially towards its other end 27, i.e. in a helical movement, the punching member 15 is forced to move in the axial direction towards the second part 9 of the outer sleeve element 71. As the guiding element 17 reaches the horizontal additional extension of the guiding groove 18, i.e. adjacent the closed end 27, the axial movement stops. As the guiding element 17 reaches the closed end 27 of the guiding groove 18, further rotation is prevented.

Figure 6C:
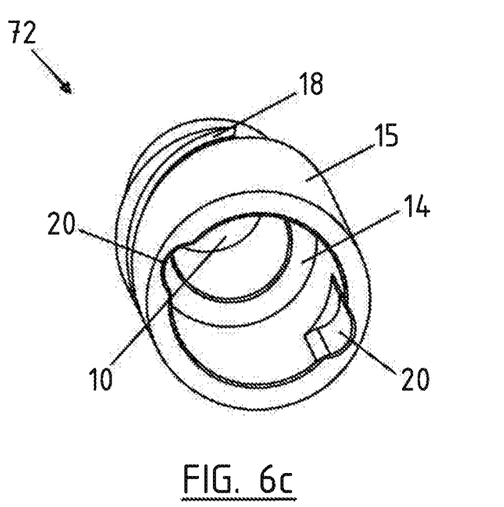
Figure 6D:
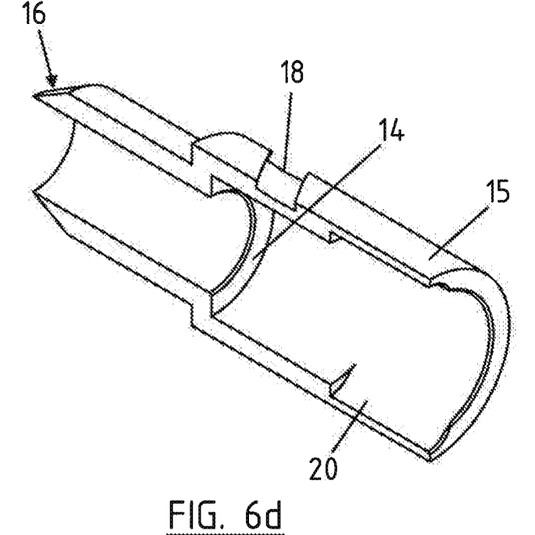
FIG. 6d shows a cross section of a perspective view of the inner sleeve element of FIG. 6a-c.

The inner sleeve element 72, exemplified as the punching member 15, is further provided with a guiding through-hole 10 that makes it capable of receiving and guiding the drill 2 (via the drill stop sleeve 12) during drilling operation, see FIGS. 2-3. The diameter of the guiding through-hole 10 is adapted to the diameter of the drill stop sleeve 12 provided upon the drill 2. A flange 14, see FIGS. 6*c-d*, extends circumferentially along the inside of the guiding through-hole 10, wherein the flange 14 defines the end position of the drill stop sleeve 12 in the guiding through-hole 10.

The flange 14 defines the axial end of a portion 24 of the guiding through-hole 10, i.e. it determines the depth of the portion 24 of the inner sleeve element 72 (the punching member 15). The maximum possible protrusion of the drilling part 3 of the drill 2 from the inner sleeve element 72 of the guiding sleeve 7 is reached when the drill stop sleeve 12 abuts the flange 14, and hence the drilling depth may be controlled by the inner sleeve element 72 of the guiding sleeve 7.

The punching member 15 is also provided with a first and a second circumferentially spaced engagement member 20, wherein each engagement member 20 is a groove arranged on the inside of the guiding through-hole 10 extending axially from the outer end of the punching member 15, and intended for engagement with complementary engagement means 28 of the rotational tool 21. The rotational tool 21 is used to provide a lever that reduces the force needed to rotate the punching member 15 in the outer sleeve element 71. This enhances the control of the axial movement of the punching member 15.

Figure 7:
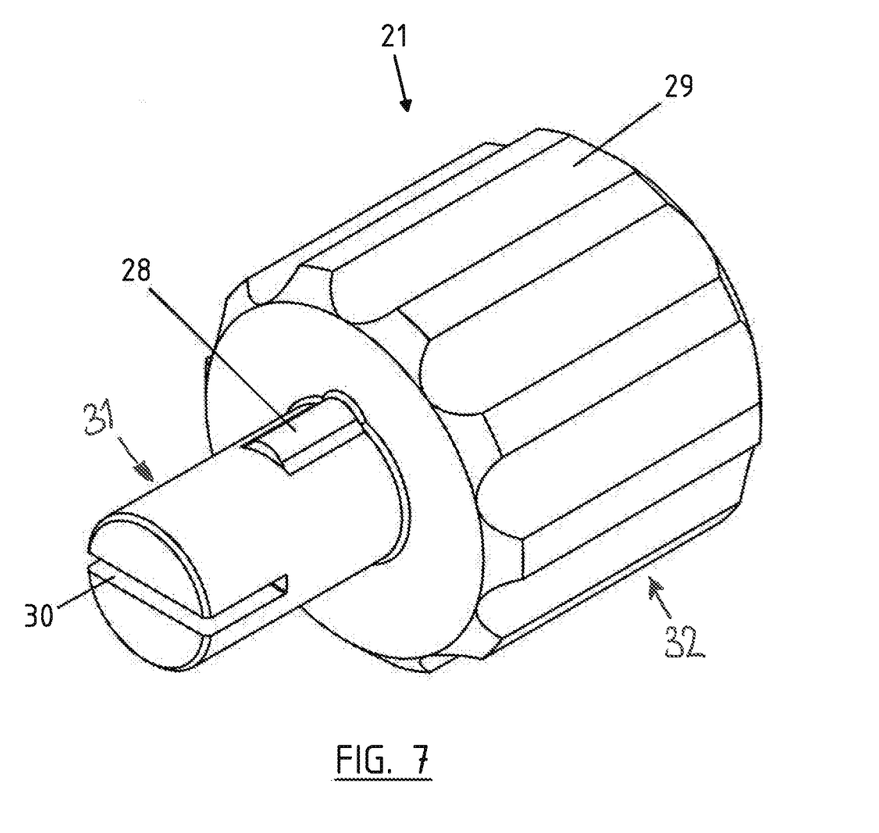
FIG. 7 shows a perspective view of the rotational tool of FIG. 1.
Figure 8A:
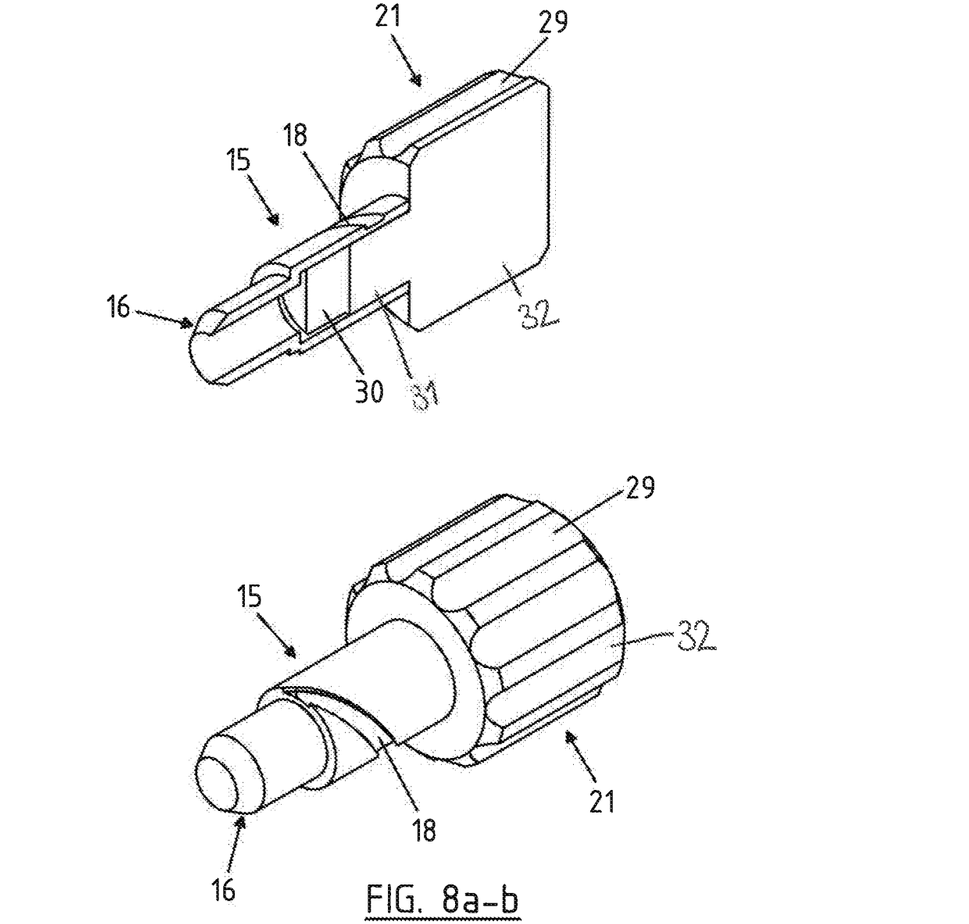
FIG. 8a shows a perspective view of the rotational tool engaged to the inner sleeve element of FIG. 1.

The rotational tool 21 seen in FIGS. 1, 7 and 8 has a first part 31 and a second part 32, wherein the first part 31 is cylindrical and the diameter is adapted such that the first part 31 fits inside the through-hole 10 of the punching member 15 of the guiding sleeve 7, as seen in FIG. 8*a-b*. The outer diameter of the first part 31 of the rotational tool 21 is essentially equal the inner diameter of the through-hole 10 such that the first part 31 of the rotational tool 21 may be received by the guiding through-hole 10 of the punching member 15. The first part 31 of the rotational tool 21 is provided with engagement means 28, shown as circumferentially spaced ridges extending perpendicular to the circumference of the first part 31 of the rotational tool 21. The engagement means 28 are spaced at the same distance as, and adapted to engage with, the engagement members 20 of the punching member 15. The free end of the first part 31 of the rotational tool 21 is further provided with a cut out 30 arranged across the cylinder diameter and extending in axial direction about half the length of the cylinder, thereby allowing the first part 31 of the rotational tool 21 to flex its diameter such that it may easily enter into the guiding through-hole 10 of the punching member 15. Thereby a rotation of the rotational tool 21 facilitates rotation of the punching member 15 relative the outer sleeve element 71.

The second part 32 has a larger diameter than the first part 31 of the rotational tool 21 and is provided with a cylindrically shaped knob facilitating manual gripping. The knob is provided with rills 29 perpendicular to its circumference which facilitates a good grip upon manual rotation of the rotational tool 21. The knob may of course be of other suitable shapes or provided with other patterns which facilitate gripping and thereby simplify the rotation of the rotational tool 21.

FIG. 2 shows the dental drill system 1 in an assembled state wherein the drill 2, with the drill stop sleeve 12 snap-locked onto it, is arranged through the punching member 15 which has been positioned in its end position in the through-hole 101 of the outer sleeve element 71 i.e. it has been guided by complementary guiding means through the outer sleeve element 71 as described in detail above. The cutting end part 16 of the punching member 15 extends from the second side 9 of the outer sleeve element 71.

FIG. 3 shows the dental drill system 1 in use; arranged in a stent 22 which is arranged upon a drilling site in a patient's mouth. The mantle surface of the outer sleeve element 71 is provided with a retention profile shown as threads (also seen in FIG. 5) which facilitate arrangement of the outer sleeve element 71 in the stent. The cutting end part 16 of the punching member 15 protrudes from the second side 9 of the outer sleeve element 71 and extends through the gum tissue 23 exposing the jaw bone 22 of a patient when in its end position, i.e. at its end axial position defined by the complementary guiding means. The outer part of the punching member 15, opposite the cutting end part 19, is arranged flush the first side 8 of the outer sleeve element 71.

The sleeve part 122 of the drill stop sleeve 12 is received in the guiding through-hole 10 in the punching member 15 such that it abuts the flange 14 arranged inside the guiding through-hole 10 of the punching member 15. The sleeve part 122 of the drill stop sleeve 12 is extending over the drilling part 3 of the drill 2. Thereby, the length of the sleeve part 122 determines the drilling depth of the exemplified drill 2. Part of the drilling part 3 of the drill 2 is protruding from the punching member 15, entering the jaw bone. Thereby the guiding sleeve 7, comprising the punching member 15 arranged in the outer sleeve element 71, function as a guide for the drill 2 during drilling operation.

The individual parts of the dental drill system 1 may be disassembled into separate parts, i.e. drill 2, drill stop sleeve 12, punching member 15 and outer sleeve element 71 after use. The individual parts may be reused, preferably after being autoclaved. The individual parts may be used separately. Also, the guiding sleeve 7 may consist of only one sleeve instead of an inner sleeve element 72 and an outer sleeve element 71.

The invention is not limited to the specific embodiment presented, but includes variations within the scope of the present claims. The guiding element may for example be a pin, a continuous thread, a broken thread or any other element suitable for being guided in a guiding groove. The elongated pin-shaped element may be a screw, a nail or any other suitable through-going element.

The term sleeve is considered to encompass various kinds of hollow cylinders.

The closed end of the guiding groove and the additional extension of the guiding groove adjacent the closed end may be arranged as a distinct bend in the guiding groove, e.g. forming a 90° pitch angle such that the end of the guiding groove extends only axial. It may also form a 180° angle such that it extends only circumferentially in a direction opposite the circumferential extension of the guiding groove. Other patterns that make up the final position in the guiding groove for the guiding element are also possible.

The axial end position of the punching member can alternatively, or as a complement, be arranged by designing the punching member and the guiding sleeve so that further axial movement is prevented by the first side of the guiding sleeve or by a flange arranged inside the guiding sleeve.

The term punching member is considered to encompass different kinds of punching elements adapted to fit in the guiding sleeve and provided with a cutting end part. For instance, the punching member does not necessarily need to be provided with a through-hole for guiding a drill or drill stop. The punching member exemplified above may also be called punching sleeve.

Reference signs mentioned in the claims should not be seen as limiting the extent of the matter protected by the claims, and their sole function is to make claims easier to understand.

As will be realised, the invention is capable of modification in various obvious respects, all without departing from the scope of the appended claims. Accordingly, the drawings and the description thereto are to be regarded as illustrative in nature, and not restrictive.

The invention claimed is:
1. A dental drill system, comprising:
    a drill having a drilling part with a first end configured for drilling a hole in a jaw bone and a shank part with a second end configured for connection to a drill-rotating device,
    a guiding sleeve for guiding the drill during drilling, and
    a drill stop sleeve that is configured for being brought onto the drill,
    wherein:
        the guiding sleeve comprises an outer sleeve element and an inner sleeve element,
        the outer sleeve element has a first side intended to face the drill-rotating device and a second side intended to face the jaw bone during a drilling operation,
        a guiding through-hole is provided in said inner sleeve element and extends at least from the first side to the second side of the outer sleeve element,
        a rim extends at least partly around the circumference of the drill,
        the drill stop sleeve is provided with a recess extending circumferentially around an inner side of the drill stop sleeve,
        a complementary guide is provided, comprising at least one guiding element located on the outer sleeve element and extending in a radial direction, and a guiding groove located on the inner sleeve element, the guiding groove being configured to receive the guiding element and guide movement of the guiding element along the guiding groove, and
        the guiding groove extends both in a circumferential direction as well as in an axial direction such that, when the guiding element and the guiding groove are engaged, a rotation of the inner sleeve element in relation to the outer sleeve element forces the inner sleeve element to move in relation to the outer sleeve element in the axial direction thereof.
2. The dental drill system according to claim 1, wherein the rim is positioned on the shank part of the drill.
3. The dental drill system according to claim 2, wherein the rim is positioned closer to the drilling part of the drill than to the second end of the shank part.
4. The dental drill system according to claim 1, wherein the drill stop sleeve is made of a high temperature resistant thermoplastic material.
5. The dental drill system according to claim 1, wherein:
    a portion of the guiding through-hole at the first side of the outer sleeve element is configured to receive the drill stop sleeve,
    the inner sleeve element comprises a flange that defines an end position for the drill stop sleeve, and
    said flange that defines the end position for the drill stop sleeve is arranged inside the guiding sleeve such as to form an end of said portion of the guiding through-hole.
6. The dental drill system according to claim 5, wherein the flange is positioned closer to the second side of the outer sleeve element than the first side of the outer sleeve element.
7. The dental drill system according to claim 1, wherein the inner sleeve element fits into and is securable in the outer sleeve element.
8. The dental drill system according to claim 1, wherein the inner sleeve element is configured to be guided by the outer sleeve element when the inner sleeve element is moved in an axial direction in relation to the outer sleeve element.

9. The dental drill system according to claim 1, wherein:
the at least one guiding element extends in the radial direction from an inside of the outer sleeve element, and
the guiding groove is arranged on an outer side of the inner sleeve element.

10. The dental drill system according to claim 1, wherein:
a pin-shaped elongated element is arranged to extend in radial direction through a hole arranged through a body of the outer sleeve element such that a tip of the pin-shaped elongated element protrudes on the inside of the outer sleeve element, and
said tip forms the guiding element.

11. The dental drill system according to claim 1, wherein an open end of the guiding groove is configured to allow introduction of the guiding element into the guiding groove.

12. The dental drill system according to claim 1, wherein the guiding groove further has a closed end that prevents further movement of the guiding element along the guiding groove.

13. The dental drill system according to claim 1, wherein the dental drill system further comprises a rotational tool configured to engage with the inner sleeve element.

14. The dental drill system according to claim 13, wherein the inner sleeve element is provided with a first and second circumferentially spaced engagement member configured for engagement with the rotational tool.

15. The dental drill system according to claim 1, wherein:
the inner sleeve element comprises a flange that defines an end position for the drill stop sleeve, and
the guiding groove has an open end that is at least in part defined by the flange.

16. A dental drill system, comprising:
a drill having a drilling part with a first end configured for drilling a hole in a jaw bone and a shank part with a second end configured for connection to a drill-rotating device,
a guiding sleeve for guiding the drill during drilling, and
a drill stop sleeve that is configured for being brought onto the drill,
wherein:
the guiding sleeve comprises an outer sleeve element and an inner sleeve element,
the outer sleeve element has a first side intended to face the drill-rotating device and a second side intended to face the jaw bone during a drilling operation,
a guiding through-hole is provided in said inner sleeve element and extends at least from the first side to the second side of the outer sleeve element,
a rim extends at least partly around the circumference of the drill,
the drill stop sleeve is provided with a recess extending circumferentially around an inner side of the drill stop sleeve,
relative dimensions of the rim and the recess are configured to allow the drill stop sleeve to be snap-locked onto the drill,
the inner sleeve element comprises a flange that defines an end position for the drill stop sleeve,
the inner sleeve element comprises a guiding groove having an open end that is at least in part defined by the flange,
the inner sleeve element and the outer sleeve element are provided with a complementary guide configured to control the axial movement of the inner sleeve element in the outer sleeve element during a punching operation,
the complementary guide comprises at least one guiding element that extends in a radial direction and the guiding groove, the guiding groove being configured to receive the guiding element and guide its movement along the guiding groove, and
the guiding groove extends both in a circumferential direction as well as in an axial direction such that, when the guiding element and the guiding groove are engaged, a rotation of the inner sleeve element in relation to the outer sleeve element forces the inner sleeve element to move in relation to the outer sleeve element in the axial direction thereof.

17. The dental drill system according to claim 16, wherein:
the rim is positioned on the shank part of the drill,
the rim is positioned closer to the drilling part of the drill than to the second end of the shank part,
a portion of the guiding through-hole at its first side of the guiding sleeve is configured to receive the drill stop sleeve,
said flange that defines the end position for the drill stop sleeve is arranged inside the guiding sleeve such as to form an end of said portion of the guiding through-hole, and
the flange is positioned closer to the second side of the guiding sleeve than the first side of the guiding sleeve.

18. The dental drill system according to claim 1, wherein relative dimensions of the rim and the recess are configured to allow the drill stop sleeve to be snap-locked onto the drill.

* * * * *